US011730933B2

United States Patent
Guirguis et al.

(10) Patent No.: US 11,730,933 B2
(45) Date of Patent: Aug. 22, 2023

(54) SURGICAL DRAIN SYSTEM AND CONTAINER

(71) Applicant: MEDTRONIC ADVANCED ENERGY LLC., Minneapolis, MN (US)

(72) Inventors: Mark Guirguis, Minneapolis, MN (US); Nathan Zamarripa, Minneapolis, MN (US); Nicholas Valley, Minneapolis, MN (US); Christian Schasel, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1002 days.

(21) Appl. No.: 15/891,936

(22) Filed: Feb. 8, 2018

(65) Prior Publication Data

US 2018/0228945 A1 Aug. 16, 2018

Related U.S. Application Data

(60) Provisional application No. 62/457,473, filed on Feb. 10, 2017.

(51) Int. Cl.
*A61M 27/00* (2006.01)
*A61M 1/00* (2006.01)
*A61F 5/44* (2006.01)

(52) U.S. Cl.
CPC .............. *A61M 27/00* (2013.01); *A61M 1/60* (2021.05); *A61M 1/64* (2021.05); *A61M 1/66* (2021.05);
(Continued)

(58) Field of Classification Search
CPC ...... A61M 27/00; A61M 1/0001; A61M 1/00; A61M 1/0009; A61M 1/0011;
(Continued)

(56) References Cited

U.S. PATENT DOCUMENTS 3,952,727 A 4/1976 Nolan
4,930,997 A 6/1990 Bennett
(Continued)

FOREIGN PATENT DOCUMENTS

AU 2014200853 3/2014
EP 2781166 B1 9/2015
(Continued)

OTHER PUBLICATIONS

Definition of Lubricious (Year: 2021).*
(Continued)

*Primary Examiner* — Nicholas J. Weiss
*Assistant Examiner* — Gabriella E Burnette
(74) *Attorney, Agent, or Firm* — Patterson Thuente, P.A.

(57) ABSTRACT

A portable drain system having a subdermal drain and a container in fluid communication with the subdermal drain is disclosed. The subdermal drain is configured to drain fluid from a surgical site. The container provides a negative pressure to the subdermal drain. The container draws and receives the fluid. The container includes at least one sensor in which the at least one sensor is configured to detect at least one of fluid color, fluid volume in the container, and orientation of the container.

56 Claims, 4 Drawing Sheets

(52) U.S. Cl.
CPC ............... *A61M 1/70* (2021.05); *A61M 1/73* (2021.05); *A61M 1/80* (2021.05); *A61M 1/90* (2021.05); *A61M 1/95* (2021.05); *A61M 1/98* (2021.05); *A61M 1/982* (2021.05); *A61M 1/984* (2021.05); *A61F 5/4404* (2013.01); *A61M 2205/103* (2013.01); *A61M 2205/12* (2013.01); *A61M 2205/18* (2013.01); *A61M 2205/215* (2013.01); *A61M 2205/3306* (2013.01); *A61M 2205/3379* (2013.01); *A61M 2205/3553* (2013.01); *A61M 2205/3561* (2013.01); *A61M 2205/3592* (2013.01); *A61M 2205/8206* (2013.01); *A61M 2209/088* (2013.01)

(58) Field of Classification Search
CPC .............. A61M 1/0003; A61M 1/0068; A61M 1/0017; A61M 1/0005; A61M 1/008; A61M 1/0039; A61M 1/0041; A61M 1/0031; A61M 1/006; A61M 1/0023; A61M 1/0078; A61M 1/0094; A61M 1/0096; A61M 1/0025; A61M 1/0086; A61M 1/0066; A61M 60/00; A61M 2209/088; A61M 2205/12; A61M 2205/8206; A61M 2205/3553; A61M 2205/3306; A61M 2205/215; A61M 2205/3596; A61M 2205/3379; A61M 2205/3561; A61F 5/4404
See application file for complete search history.

(56) References Cited

U.S. PATENT DOCUMENTS

| | | | |
|---|---|---|---|
| 5,944,703 A | | 8/1999 | Dixon et al. |
| 6,010,453 A * | | 1/2000 | Fiddian-Green ....... A61B 5/145 |
| | | | 600/309 |
| 6,695,825 B2 | | 2/2004 | Castles |
| 7,267,671 B2 | | 9/2007 | Shehada |
| 7,322,971 B2 | | 1/2008 | Shehada |
| 8,696,403 B2 | | 4/2014 | Haley |
| 8,911,765 B2 | | 12/2014 | Moses et al. |
| 9,457,129 B2 | | 10/2016 | Buevich et al. |
| 10,532,135 B2 * | | 1/2020 | Lopez ................. A61M 1/0023 |
| 10,549,016 B2 * | | 2/2020 | Bushko ............... A61M 1/0088 |
| 10,744,239 B2 * | | 8/2020 | Armstrong .......... A61M 1/0031 |
| 2004/0000349 A1 | | 1/2004 | Cull et al. |
| 2004/0116902 A1 * | | 6/2004 | Grossman ........... A61M 1/0027 |
| | | | 604/540 |
| 2006/0074484 A1 | | 4/2006 | Huber |
| 2007/0167927 A1 | | 7/2007 | Hunt et al. |
| 2008/0168836 A1 * | | 7/2008 | Wu ..................... G01F 23/0007 |
| | | | 73/313 |
| 2009/0012493 A1 * | | 1/2009 | Harig ................. A61M 1/0003 |
| | | | 604/404 |
| 2009/0293887 A1 | | 12/2009 | Wilkes et al. |
| 2010/0049150 A1 * | | 2/2010 | Braga ................. A61M 1/0049 |
| | | | 604/313 |
| 2010/0204765 A1 | | 8/2010 | Hall et al. |
| 2011/0130712 A1 | | 6/2011 | Topaz |
| 2012/0136325 A1 | | 5/2012 | Allen et al. |
| 2012/0208285 A1 * | | 8/2012 | Deighan ............. A61J 15/0084 |
| | | | 436/163 |
| 2012/0302938 A1 * | | 11/2012 | Browd ................ A61M 27/006 |
| | | | 604/9 |
| 2012/0316491 A1 | | 12/2012 | Joensson |
| 2013/0267918 A1 * | | 10/2013 | Pan ..................... A61M 1/0088 |
| | | | 604/318 |
| 2013/0327326 A1 | | 12/2013 | Brennan |
| 2013/0331805 A1 * | | 12/2013 | Brennan ............... A61M 1/008 |
| | | | 604/321 |
| 2014/0194840 A1 * | | 7/2014 | Eckermann ......... A61M 1/0025 |
| | | | 604/328 |
| 2014/0350494 A1 * | | 11/2014 | Hartwell ............. A61M 1/0088 |
| | | | 604/319 |
| 2015/0019257 A1 | | 1/2015 | Doyle et al. |
| 2015/0025485 A1 * | | 1/2015 | Luckemeyer ....... G01F 23/2967 |
| | | | 604/319 |
| 2015/0359457 A1 * | | 12/2015 | Blumenthal ......... A61B 5/1038 |
| | | | 73/172 |
| 2016/0082165 A1 * | | 3/2016 | Alvarez ............... G06Q 10/087 |
| | | | 604/74 |
| 2016/0256615 A1 * | | 9/2016 | Poormand ........... A61M 1/0003 |
| 2017/0021128 A1 | | 1/2017 | Erbey, II et al. |
| 2017/0095648 A1 * | | 4/2017 | Nowak ................ A61M 1/0011 |
| 2017/0100068 A1 * | | 4/2017 | Kostov .................. A61B 5/208 |
| 2017/0112981 A1 * | | 4/2017 | Friedman ............. A61M 39/28 |
| 2017/0128639 A1 * | | 5/2017 | Erbey, II ............. A61M 1/0035 |
| 2017/0196478 A1 * | | 7/2017 | Hunter ................ A61B 5/6847 |
| 2017/0197018 A1 * | | 7/2017 | Mukherjee .......... A61M 1/0031 |
| 2017/0281064 A1 * | | 10/2017 | Bayon ................ A61B 5/14539 |
| 2018/0000999 A1 * | | 1/2018 | Dolmatch ........... A61M 1/0017 |
| 2018/0228945 A1 * | | 8/2018 | Guirguis ............. A61M 1/0023 |
| 2018/0296737 A1 * | | 10/2018 | Sivakumaran ........ C08F 220/06 |
| 2019/0151515 A1 * | | 5/2019 | Selby .................... A61M 27/00 |
| 2020/0000979 A1 * | | 1/2020 | Myers ................... A61M 39/20 |

FOREIGN PATENT DOCUMENTS

| | | |
|---|---|---|
| TW | 201200185 A | 1/2012 |
| WO | 2014160481 | 10/2014 |
| WO | 2017148824 A1 | 9/2017 |
| WO | 2017205446 A1 | 11/2017 |

OTHER PUBLICATIONS

Chevrollier G.S., Rosato F.E., Rosato E.L. (2018) Fundamentals of Drain Management. In: Palazzo F. (eds) Fundamentals of General Surgery. Springer, Cham. https://doi.org/10.1007/978-3-319-75656-1_11 (Year: 2018).*

Regtien, Paul and Edwin Dertien, "Sensors for Mechatronics, second edition: Chapter 7: Optical sensors" pp. 183-243 (hereafter referred to as Regtien and chapter number) (Year: 2018).*

U.S. Appl. No. 62/409,400, filed Oct. 18, 2016; "Portable Device with Disposable Reservoir for Collection of Internal Fluid After Surgery"; First named inventor: Joshua Herwig.

U.S. Appl. No. 62/340,853, filed May 24, 2016; "Portable Device with Disposable Reservoir for Collection of Internal Fluid after Surgery"; First named inventor: Esra Roan.

Non-Final Office Action for U.S. Appl. No. 15/879,034, dated Apr. 9, 2020 (31 pages).

Final Office Action for U.S. Appl. No. 15/879,034, dated Aug. 4, 2020 (31 pages).

* cited by examiner

SURGICAL DRAIN SYSTEM AND CONTAINER

CROSS REFERENCE TO RELATED APPLICATION

This Non-Provisional Utility Applications claims benefit to U.S. Provisional Application No. 62/457,473, filed Feb. 10, 2017, titled "SURGICAL DRAIN SYSTEM," the entirety of which incorporated herein by reference.

BACKGROUND

This disclosure relates generally to the field of medical devices, systems and methods for use in surgical recovery after surgical procedures or medical treatment. More specifically, this disclosure relates to a portable surgical drain system having a portable container in fluid communication with an implantable drain, in which the portable container includes at least one sensor and a processing circuit.

A surgical drain is a medical device that may be used after surgery to remove accumulated bodily fluids such as pus, blood, serous fluid, or other fluids and small solids such as fibrin, clot, or other materials from a wound or surgical site. In one example, a surgical drain can be a portable medical device that includes an internal drain coupled to a fluid-collection container via tubing. Examples of portable drains can be active drains or passive drains of various sizes. Active drains can be attached to a suction source, such as closed-suction drains. Passive drains have no suction source and work according to the differential pressure between the body cavity and the exterior.

A Jackson-Pratt drain is one example of a closed-suction portable medical device that is commonly used as post-operative drain for collecting bodily fluids from closed spaces that may cause either disruption of the wound and healing process or become an infected abscess. Either scenario may require a formal drainage or repair procedure and possibly another visit to the operating room. Portable closed-suction drains can be applied to various surgical sites such as abdominal surgery, breast surgery including mastectomies, thoracic surgery, joint replacements, and craniotomies. Additionally, such drains can be used to evacuate an internal abscess before surgery when an infection already exists.

A closed suction can be provided with a flexible grenade-shaped bulb fluid-collection container. The patient, caregiver, or healthcare provider can squeeze the air out of an empty bulb and attach the tubing to the surgical drain before releasing the bulb. The resulting vacuum creates suction in the tubing and drain, which gradually draws fluid from the surgical site into the bulb. The bulb may be repeatedly reopened to remove the collected fluid and squeezed to restore suction.

Typically, the patient or caregiver is tasked with examining the fluid for signs of possible infection or blood and to accurately measure and record the drainage output. Handling of the drain system is a potential source of infection, and a requirement of self-monitoring the fluid is susceptible to patient or caregiver error or inaccuracies, which can lead to complications and ineffective treatment.

Drain systems, such as Jackson-Pratt drains, have a tendency to become clogged or occluded with fibrin, clot, or other material. This results in loss of drain patency and thus fluid, blood or infected material can build up in the wound resulting in a wound hematoma, abscess, infection, or other complication. The patient or caregiver is also tasked to make sure the drains do not clot or become clogged when they are still in use. This risk can be reduced by a daily subcutaneous injection of low-molecular-weight heparin until the surgical drain is removed. Once a drain becomes clogged or occluded, it is usually stripped by hand to remove the clog. The drain system may be removed if stripping is unsuccessful, as it no longer provides any benefit.

SUMMARY

This summary is provided to introduce a selection of concepts in a simplified form that are further described below in the Detailed Description.

In one aspect, the disclosure is directed to a portable drain system having a drain in fluid communication with a container. The drain is configured to drain fluid from a wound or surgical site and the container collects the fluid. In one example, the drain is a subdermal drain implantable in a patient's body and the container is worn on the outside of the body. The drain system includes sensors to detect one or more of fluid color, fluid volume, and orientation of the container. The one or more sensors can be provided to a processing circuit that can include a processor. Volume of the drainage fluid can be detected at multiple times to determine an amount of fluid flow with the processor. In one example, the processor can detect sensor signals representative of drainage fluid volume at times that the container is in a selected orientation, such as upright. In one example, the one or more sensors and processing circuit are located on the container.

In another aspect, the disclosure is directed to a portable drain system having a clog remover system. In one example, the one or more sensors can be applied to detect clogs in a lumen from the drain to the container. For instance, the processing circuit can inferentially determine a clog is present if fluid volume has not changed or has not changed an expected amount over a selected period of time. If a clog is detected, the processing circuit can operate a clog remover for a selected amount of time to remove the clog. In one example, the clog remover includes a turbine in the lumen that will rotate about an axis to loosen and/or release the clog. In another example, the clog remover system is operated without the processing system, such as the turbine is constantly operating while the container is configured to receive fluid.

In another aspect, the disclosure is directed to a portable drain system having wireless-network communication features. For example, the processing circuit is operably coupled to a communications module on the drain system, such as on the container. The communications module is configured to transmit computer data via a wireless-network, such as wireless local area network or wireless personal network, to a computing device or network intermediary. The computing device or network intermediary is configured to transmit data related to the computer data to a remote server. In one example, the data related to the computer data on the remote server is accessible via a browser-based application. In one example, the processing circuit provides notifications to the user via the computing device and to a clinician via the remote server. For instance, the processing circuit can alert the patient's smart phone or laptop that the container is filled with fluid. In some examples, the clog remover or other features of the container or portable drain system can be operated remotely via the wireless-network communication features such as via a computer application operated by the patient or a caregiver.

In another aspect, the disclosure is directed to an active portable drain system. The container can include a drain hub and a replaceable cartridge. In one example, the drain hub includes at least one of the one or more sensors, the processing circuit, the communications module, and the clog remover. The cartridge is configured to receive the fluid in a vessel and can be replaced, such as when the cartridge is full. In one example, the cartridge is disposable. In one example, the vessel is provided with a prescribed vacuity such that a differential pressure between the surgical or wound site and vessel is established when the cartridge is inserted into the drain hub to draw fluid into the container.

The drain systems can use sensors to detect, analyze, and relay pertinent information to both patients and physicians. Sensors can provide information on collected volume of serous fluid, rate of serous fluid collection, color of serous fluid, and suction pressure applied to wound cavity. Analysis of volume and rate of fluid collection of the serous fluid can provide information correlating to the healing process and the time when drains can be removed from the patient. Additionally, information such as color of serous fluid may correlate to infection. In one instance, an unexpected change of serous fluid color along with an increase in serous fluid excretion may be indicative of an infection or of a patient not healing properly. Sensing suction pressure allows for the drain system to apply an optimal and controlled suction profile to the wound cavity to promote healing.

Measurement of collected fluid volume is vital to determining a variety of factors including drain health and effectiveness, wound healing condition, presence of infection, predicting seroma formation, and when to remove the drain from the patient. Typically, fluid is poured or otherwise transferred from the collection bulb to a graduated cup where the volume is then manually read and recorded after which the fluid is discarded, commonly in the toilet or down the drain of a sink. This process of intimately dealing with the drainage fluid is almost always uncomfortable for patients, and is many times a traumatic experience. Additionally, as this volume measurement is the largest factor influencing drain removal times, patients can intentionally bias the measurements to have their drains removed prematurely, placing them at elevated risk of adverse effects, namely formation of seromas. As such, the drain system provides several methods of fluid volume measurement.

In one example, the disclosure includes portable drain system comprising a subdermal drain and a pumpless container in fluid communication with the subdermal drain. The subdermal drain is configured to drain fluid from a surgical site. The pumpless container provides a negative pressure to the subdermal drain. The pumpless container draws and receives the fluid. The container includes at least one sensor in which the at least one sensor is configured to detect at least one of fluid color, fluid volume in the container, and orientation of the container.

"Pumpless," in this disclosure means the drain system, the container in the drain system, or a cartridge, which is a component of the container to draw and receive fluid, does not use a mechanical pump to move fluid along a pathway from the surgical site into the container. A mechanical pump can include a positive displacement pump such as a peristaltic pump and uses some mechanism that consumes energy to produce work that moves the fluid. For example, a pumpless cartridge, container, or drain system draws fluid via a source of negative pressure such as a prescribed vacuity instead of using a mechanical pump in the cartridge, container, or drain system. In one example, the entire drain system, the container, or the cartridge can be pumpless. A negative pressure is a pressure less than ambient or the pressure at the surgical site, which is appropriate.

In one example, the disclosure includes a portable drain system having a subdermal drain and container in fluid communication with the subdermal drain. The subdermal drain is configured to drain fluid from a surgical site of a patient. The container provides a negative pressure to the subdermal drain, in which the container draws and receives the fluid. The container includes at least one sensor in which the at least one sensor is configured to detect at least one of fluid color, fluid volume in the container, and orientation of the container. The drain includes a suction member in fluid communication with the container and an inflatable balloon isolated from fluid communication with the container.

In one example, the disclosure includes a container for a portable surgical drain system to receive a fluid from a drain at a surgical site. The container includes a drain hub having a sensor and a pumpless cartridge removably coupled to the drain hub in fluid communication with the drain to draw and receive the fluid from the surgical site. The sensor includes an array of photodiodes on the drain hub to detect fluid volume in the cartridge.

In one example, the disclosure includes a container for a portable surgical drain system to receive a fluid from a drain at a surgical site. The container includes a drain hub having a sensor and a pumpless cartridge removably coupled to the drain hub in fluid communication with the drain to draw and receive the fluid from the surgical site. The sensor includes a set of light filtered photodiodes and a light source on the drain hub to detect color of the fluid in the cartridge.

In one example, the disclosure includes a container for a portable surgical drain system to receive a fluid from a drain at a surgical site. The container includes a drain hub having at least one sensor and a processing circuit operably coupled the at least one sensor. The container also includes a pumpless cartridge removably coupled to the drain hub in fluid communication with the drain to draw and receive the fluid from the surgical site. The at least one sensor detects at least one of fluid color and fluid flow, and the processing circuit is configured to provide an alert of a change in fluid color or increase in fluid flow.

In one example, the disclosure includes a container for a portable surgical drain system to receive a fluid from a drain at a surgical site. The container includes a drain hub having a plurality of sensors and a cartridge removably coupled to the drain hub in fluid communication with the drain to draw and receive the fluid from the surgical site. A first sensor of the plurality of sensors includes a first volume sensor to detect volume of the fluid when the cartridge is in a first orientation. A second sensor of the plurality of sensors includes a second volume sensor to detect volume of the fluid when the cartridge is in a second orientation. A third sensor of the plurality of sensors is an inertial motion sensor to detect whether the cartridge is in the first orientation or the second orientation.

In one example, the disclosure includes a container for a portable surgical drain system to receive a fluid from a drain at a surgical site. The container includes a drain hub having at least one sensor. The cartridge also includes a cartridge having a generally rigid vessel. The cartridge is removably coupled to the drain hub in fluid communication with the drain to provide a pumpless suction source to draw the fluid from the surgical site into the vessel. The at least one sensor is configured to detect a characteristic of the fluid in the vessel.

DETAILED DESCRIPTION

Figure 1:
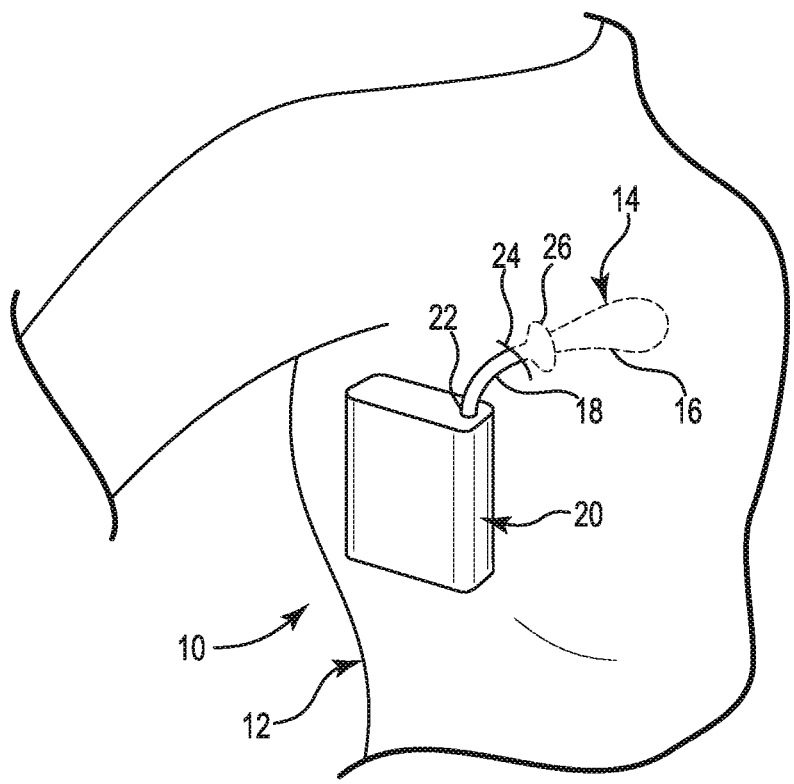
FIG. 1 is a front view of an example environment of an example drain system coupled to a patient's body.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a wound or surgical site.

FIG. 1 illustrates an example environment for an example surgical drain system 10. The surgical drain system 10 is configured to include a portion for implantation within a patient's body 12 proximate the surgical or wound site 14 of interest. In the example environment of FIG. 1, the surgical drain system 10 is implanted in the patient's torso to drain serous fluid resulting from a mastectomy. Other example environments and surgical sites are contemplated. In one example, the drain system 10 is portable such that it carried on the body, configured to travel with the patient, and does not generally interfere with a patient's mobility. For example, the portable drain system 10 can be worn on the body and carried from location to location, including locations away from a care facility. In one example, the portable drain system 10 can continue to communicate with clinicians at a care facility when worn in remote locations.

The drain system 10 includes an implantable drain 16, which can be selected from one or more drains particularly configured to be positioned at the surgical or wound site 14, in fluid communication with a fluid-collection container 20 via tubing 18. In one example, the tubing 18 may be integrally formed with the drain 16 and coupled to the container 20 or a separate piece that is coupled to the drain 16 and the container 20 at a distal end 22 of the tubing 18. The drain includes a suction member having one or more openings on an outside surface in fluid communication with an inside surface of the drain. The suction member in the example, is located near a proximal tip of the drain system 10. The drain 16 and tubing 18 form a lumen such that fluid from the surgical or wound site 14 is drawn into the drain 16 via the openings on the outside surface of the suction member and into the lumen in fluid communication with the inside surface of the drain. The fluid is thus transported distally into the container 20 via the tubing 18 by way of an active or passive process associated with the drain system 10.

In the example of mastectomy, the drain 16 can be a standard subdermal drain positioned proximate the pectoralis major muscle at the surgical site 14 inside the patient. The patient's body 12 may include one or more drain incisions 24 for the tubing 18 to extend into the body 12 to the surgical site 14. The container 20 can be positioned outside of the body 14 against the torso such as proximate the under arm. More than one drain systems may be used on a patient at a time. The drain system 10 can be carried on the body via straps, a holster, brace, pockets on a general or specialized clothing article, tape, other attachment mechanism.

In a typical drain fixation, two non-resorbable surgical sutures are placed at the percutaneous drain exit site or drain incision 24. The sutures pierce the skin and are tied of around the circumference of the drain using "air knots" so as not to restrict the drain 16 or tubing 18. In addition to the sutures, surgical tape or a surgical dressing may be placed over the incision 24. This approach presents several challenges including patients often complain of pain at the surgical site, the surgical site often presents itself as red, irritated skin, leading to concerns of infection, and perhaps most concerning when the patient catches the drain system 10 on something while moving about, which can tear the sutures from the skin. In the illustrated example, the drain 16 includes an inflatable balloon 26 inside the incision 24 to secure the drain 16 in place. In the example, the inflatable balloon is distal the suction member of the drain 16. The drain 16 is installed into the patient with a deflated balloon 26 placed inside the patient inside the incision 24. The balloon 26 is inflated with a fluid to hold drain 16 in place. The balloon 26 can be deflated prior to removal from the patient. In one example, the drain 16 or tubing 18 can include a separate lumen in fluid communication with the balloon 26. This separate lumen can be isolated from the lumen in fluid communication with the container 20, or not in fluid communication with the container 20. The separate lumen (not shown) in fluid communication with the balloon 26 can include a valve outside of the patient. A clinician can open the valve and couple the separate lumen to source of positive pressure to fill the balloon 26 to a selected amount of fluid, and then close the valve to leave the balloon 26 inflated. The clinician can later open the valve to deflate the balloon 26.

The drain system 10 can be constructed from materials configured to reduce the chance of irritation and other complications. The drain 16 and tubing 18 may be constructed from any material suitable for implantation with the body 12, and the material may be selected to reduce the chances of allergy or other reaction. For example, the material may be of a biocompatible silicone, polyether ether ketone (PEEK), polyvinyl chloride (PVC), polytetrafluoroethylene (PTFE), or other material. The tubing 18 may be formed from PVC, PEEK, or a thermoplastic elastomer (TPE) such as a polyether block amine (PEBA). Aspects of the drain system, such as the tubing 18 or drain 16 can include a hydrophilic or lubricious coating, for example, to assist in removal from the surgical site 14 or drain incision 24. The drain 16 and tubing 18 can include an outside surface facing or in contact with the patient and in inside surface, such as a lumen wall. In one example, both the outside and inside surfaces include a hydrophilic or lubricious coating. A coating on the inside surface can reduce drag and shear force coefficients, which can lead to improved fluid flow. A coating on the outside surface can decrease friction upon removal of the drainage system from the patient. Additionally, the drain 16 and tubing 18 can include antimicrobial agents to reduce the likelihood or effect of seroma and surgical site infections. For example, the drain 16 and tubing 18 can be manufactured as extruded with the antimicrobial agents. In another example, antimicrobial agents can be applied to the drain 16 or tubing 18, such as during manufacture or subsequent to manufacture. Still further, the drain 16 and tubing, such as the inside surfaces of the drain 16 and tubing 18 can include a coating to reduce the likelihood of formation of fibrin clots or masses of coagulated proteins. For example, the inside surface of the drain 16 or tubing 18 can include a coating including heparin. Loaded levels of the coating could be selected such that backflow or diffusion of the coating into the patient would be inconsequential to healing and would not affect patient health. In one example, the heparin coating is available under the trade designation Astute from BioInteractions, Ltd., of Reading, UK, which can repel proteins and blood cells through negative charge repulsion, and further reduce adhesion due to utilization of polyethylene glycol (PEG) polymers.

The drain 16 or tubing 18 proximate the drain incision 24 can include a drug-eluting sleeve on the outside surface. In one example, the sleeve may be made of a biodegradable polymer that eludes controlled dosage of drugs for antibiotic, anti-inflammatory, or other medically helpful purpose. The sleeve could be configured such that the outside surface has a neutral or negative draft angle with reference to the skin surface such that the portion within the patient is the same or smaller in diameter than the portion at the skin surface. For example, the outer diameter of the drain 16 or tubing is greater distal to the inflatable balloon 26 than the outer diameter of the drain 16 proximal to the inflatable balloon.

In the example, the container 20 includes a smooth wall design without sharp corners to cut or pinch the body 12 as well as a low profile to tuck neatly under the arm or against the body 12 to help conceal the drain system 10, fit under clothes, not restrict movement, and reduce discomfort. The container 20 may include an ergonomic design to reduce irritation and promote comfort, and it may be constructed from a synthetic polymer outer surface or have a polymer shell, coating or a removable cover such as polycarbonate, acrylonitrile-butadiene-styrene (ABS), or other material. As indicated in the example, the features of the container 20 can be incorporated into a single, unitary block or piece without attachments or accessories to promote a stable, ergonomic object. In one example, the container 20 is generally fluid tight, constructed of a water tight or fluid tight material and having fluid tight junctions and possibly seals at all junctions. Similarly, the container 20 in combination with the tubing 18 is also fluid tight so that, in one example, a patient can bathe or shower while wearing the drain system 10 without causing damage to the internal components of the container 20 or malfunction of the drain system 10.

Figure 2:
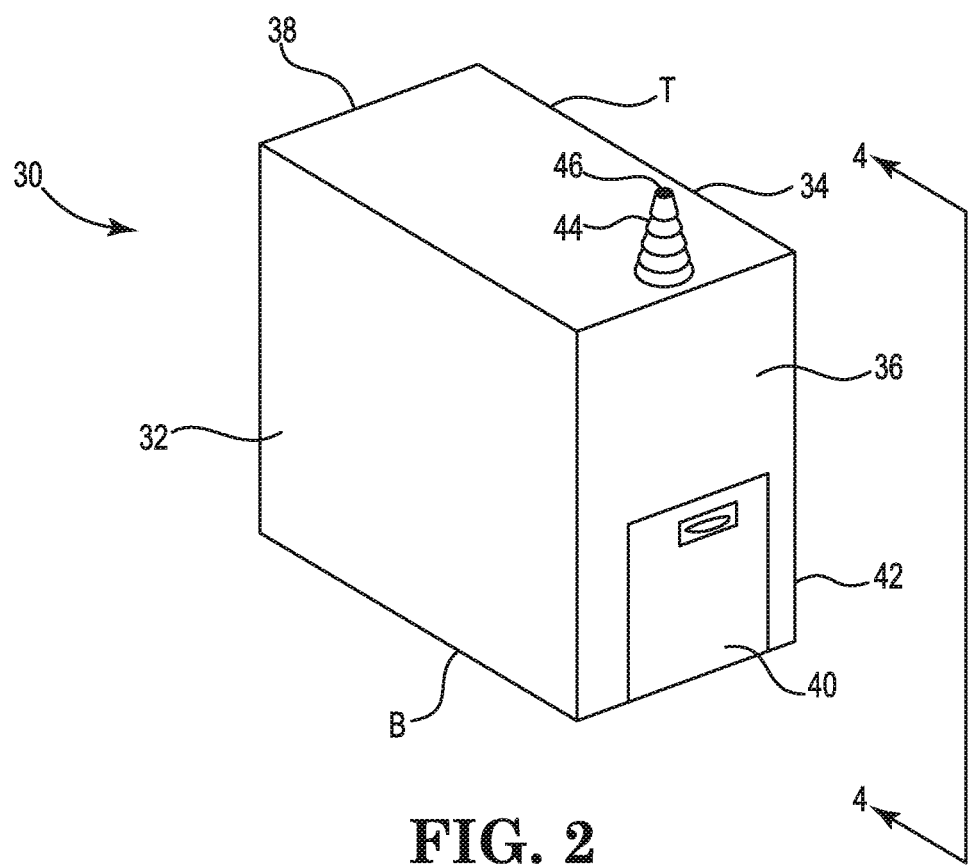
FIG. 2 is a perspective view of an example container of the drain system of FIG. 1.

FIG. 2 illustrates an example container 30, which can be an example of container 20 of drain system 10. Container 30 can include a top surface T, or side configured to be proximate the surgical site 14, and an bottom surface B opposite the top surface T, or side configured to be distal from the surgical site 14. The container 30 can also include a pair of opposing major surfaces 32, 34, wherein one of the major surfaces 32, 34 can configured to be positioned against the patient's body 12. In some examples, the major surfaces 32, 34 can be curved or formed for comfort, such as one major surface can be concave and the other convex, generally flat, or some combination of the two. The container 30 can also include a pair of opposing side surfaces 36, 38.

The container 30 includes cartridge 40 removably coupled to a drain hub 42. The drain hub 42 includes a drain connection 44 having a fluid port 46 in fluid communication with the cartridge 40. The drain connection 44 can be configured to be removably secured to the tubing 18 such that the fluid port 46 is fluidically coupled to the drain 16. In the example, the drain connection 44 can include one or more barbs to removably secure the tubing to the container 30. The fluid port 46 is fluidically coupled to a fluid pathway 48 within the drain hub 42 that is in fluid communication with the cartridge 40. Fluid received at the fluid port 46 can travel via the fluid pathway 48 into the cartridge 40 and be received into the cartridge 40. As indicated in the example, the removable cartridge 40 can be contained within or substantially within the drain hub 42. For example, the opposing major surfaces 32, 34 can extend distally to the bottom surface B of the container 30, which can be formed by the cartridge 40. The length of the bottom surface B between side surfaces 36, 38, and width of the bottom surface B major surfaces 32, 34 can be contained within or substantially within the dimensions of the opposing major surfaces 32, 34. In the illustrated example, the drain connection 44 is included on the top surface T and extending generally perpendicular from the top surface T, although other configurations or locations for the drain connection 44 are contemplated.

In the examples, the drain hub 42 can include sensors, circuitry, and a power source, such as a battery. In some examples, the drain hub can include a mechanism to remove clogs that may be powered by the battery or the source of negative pressure. The mechanism to remove clogs can be disposed within the fluid pathway 48 or form at least part of the fluid pathway 48. The cartridge 40 can collect fluid drained from the patient as well as provide a source of negative pressure to draw fluid into the container 30. Sensors of the drain hub 42 may detect parameters of the fluid from outside of the cartridge 40 or outside the surfaces of the cartridge 40 and not contact the fluid.

Figure 3:
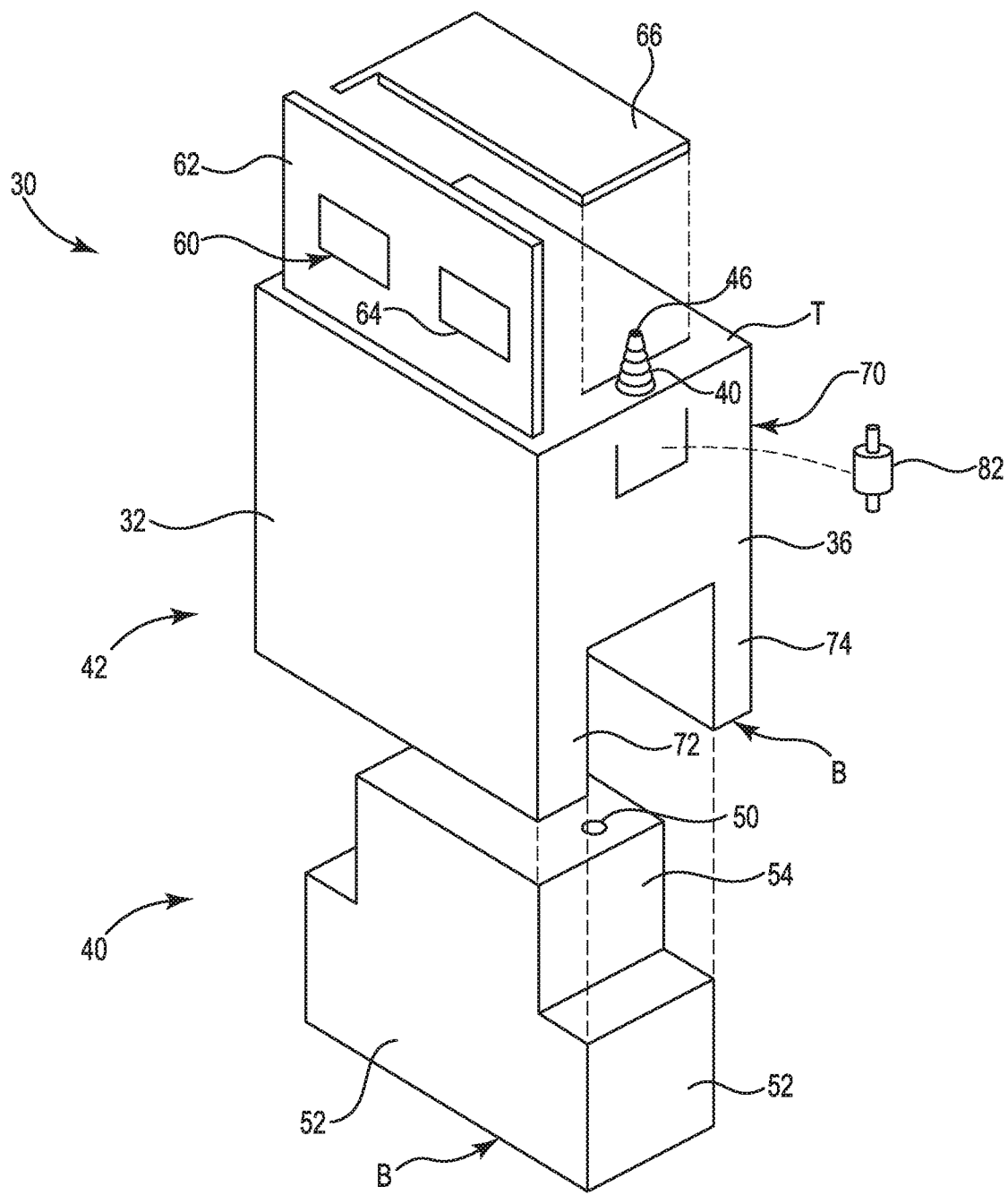
FIG. 3 is an exploded view of the container of FIG. 2.

FIG. 3 illustrates an exploded view of the portable container 30. In one example, the cartridge 40 is removably coupled to the drain hub 42 via clips or other releasable fastener mechanisms, such as on the insides of the major surfaces 32, 34. For example, a user may squeeze the drain hub 42 or pull the cartridge 40 away from the drain hub 42 in such as way as to release the cartridge 40. The cartridge 40, when released from the drain hub 42, may be emptied and returned to the drain hub 42 to receive additional fluid or replaced with a new cartridge to receive additional fluid. In one example, the cartridge 40 includes an opening 50 and a set of walls 52 surrounding a vessel 54 configured to receive the fluid. When the cartridge 40 is installed in the drain hub 42, the opening 50 is configured to be in fluid communication with the fluid port 46 and fluid pathway 48 to receive fluid into the vessel 54. The cartridge 40 can include translucent, including transparent, walls 52 or include a translucent or transparent section of one or more walls 52 to allow sensors on the container 30 such as drain hub 42 to detect features of the fluid in the vessel 54, such as color of the fluid or volume of the fluid. In one example, the entire vessel 54 is constructed from a translucent material. In another example, the surfaces of the vessel that are exposed to the outside when installed in the drain hub 42 are opaque in order to detect color or other information regarding the fluid in some configurations. For example, the cartridge may have opaque sides except for one or two translucent sides that are configured to fit against the opposing major surfaces 32, 34 of the drain hub 42.

In one example of an active drain system 10, the vessel 54 can be provided with a prescribed vacuity such as a pressure less than ambient pressure, and is sealed at the prescribed pressure prior to installation into the drain hub 42. For example, the walls 52 are generally rigid, as opposed to pliable and collapsible under the negative pressure, and a prescribed vacuity is preset at a factory or otherwise by sealing the opening 50 with a cover. The drain hub 42 can be provided with a mechanism or article, such as on the fluid pathway 48, to pierce the cover of the opening 50 when the cartridge 40 is installed into the drain hub 42. The fluid pathway 48 can include components such as O-rings or other features to help seal the fluid connection between the fluid pathway 48 and the cartridge 40. A differential pressure is created between the surgical or wound site 14 and the vessel 54 to draw fluid from the wound site 14 into the vessel 54. In one example, the particular cartridge 40 selected for attachment to the drain hub 42 can be chosen based on the vacuity of the cartridge 40 appropriate for the application. Cartridges may be manufactured with selected vacuities, and some vacuities may be preferred for some applications. Once the cartridge 40 is installed into the drain hub 42 such that a fluid connection is made with the opening 50 and the fluid pathway 48, the container 30 provides a source of negative pressure to begin to draw fluid into a drain, such as drain 16. In some examples, the opening 50 can include a one-way valve to prevent spillage when a cartridge 40 is removed from the drain hub 42.

The cartridge 40 including the vessel 54 provided with the prescribed vacuity provides several advantages over other drain systems. As compared to Jackson-Pratt drains, the vessel is preloaded to the appropriate vacuity and the patient or clinician does not manually attempt to set or create the vacuum in the bulb. Further, manually creating a vacuum on a Jackson-Pratt drain after it has been emptied of fluid can be messy, which is avoided with a new cartridge 40. Also, the present drain system 10 avoids the bulk, weight, noise, heat, and high power requirements of mechanical pump-based systems, such as peristaltic pumps. Drain systems with peristaltic pumps may include additional insulation to protect the patient from heat or noise of the pump and either include large batteries to power the pump or include frequent electrical coupling to an external power source to recharge the drain system, which includes added circuitry and size.

Another example of implementing the prescribed vacuity or negative pressure within the cartridge 40 includes a cartridge having two generally rigid chambers linked fluidically via a vacuum regulating valve. For instance, the cartridge can include two separate, discrete chambers or one chamber partitioned into two subdivisions that share a common bulkhead wall including a primary chamber to collect fluid and a secondary chamber. The primary chamber supplies down-regulated vacuum pressure, such as 400-500 mmHg abs, to the drain 16, and acts as a reservoir for the extracted fluid. The secondary chamber is a supply of high-vacuum pressure, such as less than 300 mmHg abs, to supply negative pressure to the primary chamber to maintain a relatively continuous therapeutic pressure within the wound cavity. In still another example, the primary chamber is disposed within the secondary chamber. The primary chamber is a reservoir to collect the fluid and the secondary chamber delivers negative pressure to the drain system 10. In one example, the secondary chamber is deformable to generate the negative pressure. The deformation increases the differential in volumes between the inner and outer chambers of the cartridge, with the internal volume of the outer container being greater than the (non-fluid filled) volume of the inner container.

Still further, the negative pressure could be provided to the generally rigid cartridge 40 via a spring or yieldably urgable flexible membrane that can actuate an expandable chamber within the cartridge 40. For example, the cartridge 40 can include a vessel having an internal wall that can be moved from a first position of a first volume within the vessel to a second position of a second volume within the vessel in which the second volume is greater than the first volume. The expanding volume generates the negative pressure within the cartridge. The spring or flexible membrane can be actuated by the patient or the clinician.

The cartridge 40 can include one or more chemicals to detect properties of the fluid. In one example, a self-quenching fluorescent dye, such as carboxyfluorescein, can be loaded into polymer-shelled microspheres in which the polymer shell is selectively affected by certain bacterial endotoxins, metabolic byproducts, presence of certain human immune cells, or deviations in local chemistry caused by presence of such chemicals, such as pH. For example, one or more dyes are included such as preloaded into the reservoir either loosely or within a fluid-permeable sub-reservoir within the vessel space such that drainage fluid is allowed to contact the microspheres. In another example, the dyes can be loaded into a coating, which is applied to coat the inner surface of the drainage fluid vessel, and is sensitive to bacterial presence or chemical properties as described. Additionally, certain self-quenching dyes can be selected or engineered to bind to bacterial endotoxins, metabolic byproducts, antibodies, or respond to deviations in local chemistry cause by presence of such chemicals, such as pH. In one example, the cartridge can be removed and placed into an assay device for evaluation. The cartridge is evaluated for presence and/or intensity of fluorescence at the specific wavelengths of the dye utilized within the reservoir. The assay device can be operably coupled to a repository of patient information, such as a memory device with patient data on a computing device.

FIG. 3 also illustrates the drain hub 42 includes circuit components 60, such as a printed circuit board 62 having a one or more circuit elements and electrical pathways to operably couple the circuit elements to one or more sensors 64 located on the drain hub 42. The circuit components 60 may be arranged on one or more printed circuit boards, such as circuit board 62. In one example, circuit components 60 include a processing circuit and a communications module including one or more integrated circuits described in greater detail below. The drain hub 42 can also be configured to receive a power source 66, such as rechargeable battery or a removable battery, to provide electrical power to at least the circuit elements. The drain hub 42 can include buttons, membrane switches, or other user interface mechanisms (not shown) operably coupled to the circuit components 60 to the to allow a user to control aspects of the drain system 10. The drain hub 42 can also include lights, such as light emitting diodes, or other alert mechanisms (not shown) to provide alerts or notifications to the user regarding the status of the drain system 10. Buttons and lights can be provided on one or more of the surfaces B, T, 32, 34, 36, 38.

In the illustrated example, the drain hub 42 can include a top receiver 70 proximate the top surface T including the drain connection 44, a first side 72 or first wall and a second side 74 or second wall. First and second sides 72, 74 can form major surfaces 32, 34. In the example, at least one of the first side 72 and second side 74 can be formed as hollow walls or walls having an internal structure to receive the printed circuit board 62 and one or more sensors within its interior. Power source 66 can be included in the top receiver 70. The cartridge 40 can be received in drain hub 42 between first and second sides 72, 74 and into top receiver 70. The sides 72, 74 and top receiver 70 can be formed from a rigid material to protect the circuit components 60 and power source 66 as well as to couple to the cartridge 40 such as at the rigid walls 52 of the cartridge 40.

Figure 4:
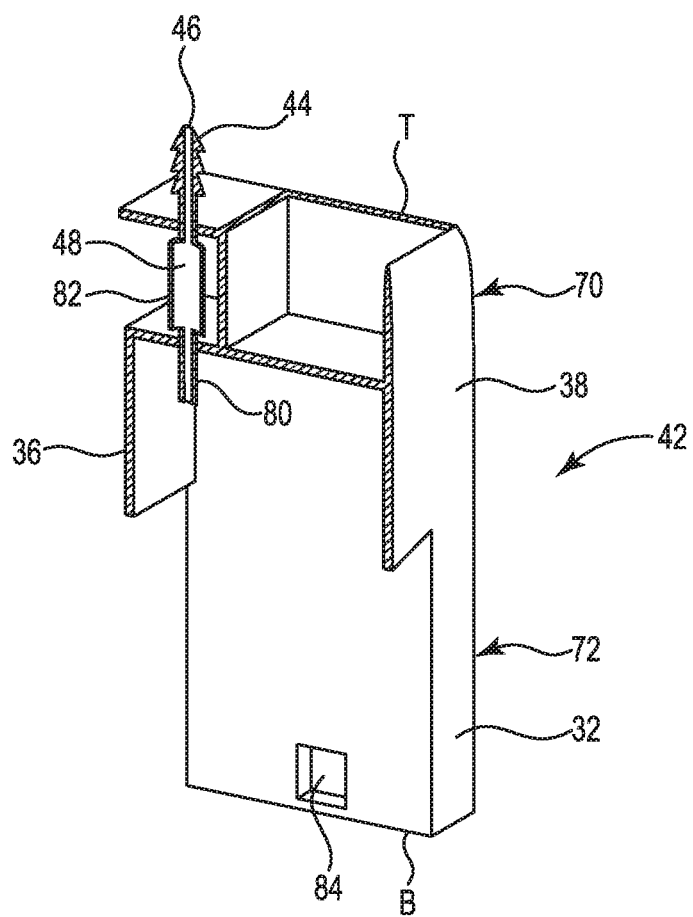
FIG. 4 is a perspective view of a section of an example drain hub of the example container of FIG. 2.

FIG. 4 illustrates a sectioned view of the drain hub 42 taken along lines 4-4 on FIG. 3. FIG. 4 provides a view of fluid pathway 48, which extends from drain connection 44 into a tube 80 that can be configured to pierce a seal in opening 50 and be in fluid communication with vessel 54 of cartridge 40. Fluid pathway 48 can include a turbine 82 that can spin to remove clogs in a fluid path between the drain 16, tubing 18, and fluid pathway 48. In the illustrated example, the turbine 82 can spin along an axis of the fluid pathway 48, although a turbine can be included to spin about another axis. The turbine 82 can be activated by the differential pressure between the vessel 54 and the drain site 14 or be separately powered and activated by circuit components 60.

In an indicated example, the turbine 82 can include an axially-extending hub or boss along the path of flow with a plurality of radially extending fins or blades. The example indicates the fins or blades extend along the side of the hub or boss along a generally straight line in the direction of the axis. Other configurations are contemplated. For example, the fins or blades can be coiled around the hub in a screw-like configuration. Additionally, the fins or blades can be in the shape of propeller blades. The turbine 82 can be disposed within a lumen forming a fluid pathway 48. The rotation of the turbine 82 can disrupt the fluid flow and loosen clogs or the rotation of the blades can generate a thrusting force in the fluid similar to a ship's propeller to dislodge clogs. In other examples, the hub or boss can be axially-extending walls of a hollow cylinder forming a lumen. The cylinder can be open at both ends, and the inner surface of the walls can include inwardly radially extending fins or blades. The fins or blades can extend along the axis in a straight line or be configured like an impeller or other similar device. Fluid can flow through the lumen formed by the hollow walls of the cylinder. In this example, the hollow cylinder can be disposed within the lumen of the forming the fluid pathway or the lumen formed by the hollow cylinder can form the fluid pathway 48.

In one example, the drain system 16 can be provided with a separate system to dislodge clogs. For example, the lumen in fluid communication with the drain 16 and fluid pathway can be coupled to a separate source of negative pressure that may be at a greater amount of negative pressure than the cartridge 40. In one example, this separate source of negative pressure can selectively replace the cartridge 40 to dislodge the clog. This separate source of negative pressure can include a peristaltic pump that can work clogged materials through the tubing. In another example, the tubing may be disconnected from the drain hub 42, such as at the drainage connection 44, and coupled to the separate source of negative pressure until the clog is dislodged. In still another example, the separate source of negative pressure can include an accessory reservoir that can be coupled to the fluid pathway 48 and activated via a valve.

In the illustrated example, at least one sensor window 84 can be included on the interior of a side 72, 74 of the drain hub facing the cartridge 40 and proximate the bottom surface B. A color sensor can be installed in the drain hub 42 proximate the sensor window 84 to detect color of the fluid in the vessel 54 through a translucent wall 52. The size and shape of the sensor window 84 is illustrated as an example, and other sizes or shapes are contemplated. For example, the sensor window 84 can extend longitudinally substantially from the bottom surface B toward the top surface T proximate the level of the tube 80. The sensor window 84 can extend along an axis that can be detected as being perpendicular to the ground or other point or points of orientation. The interior of a wall 72, 74 can include addition sensor windows to detect other features of the fluid such as volume. An array of photodiodes can disposed in the drain hub 42 within the sensor window 84, particularly if the sensor window has a length along an axis that can accommodate more than one photodiode, to detect the presence of a fluid within the cartridge 40 or a volume of the fluid within the cartridge 40.

Figure 5:
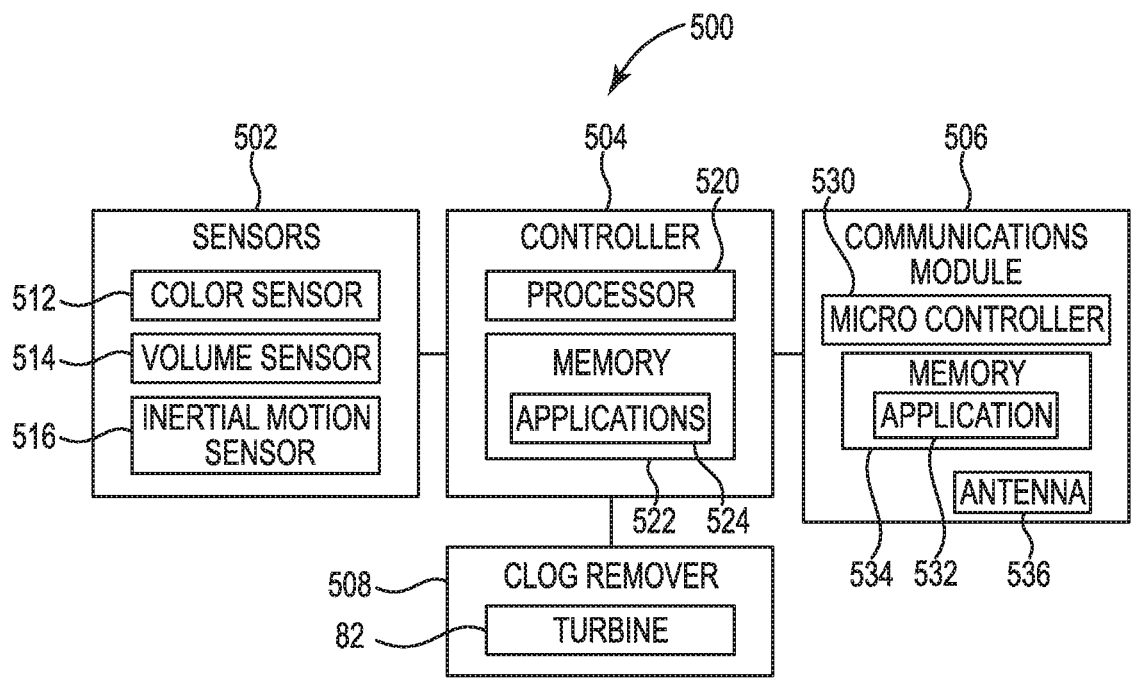
FIG. 5 is a schematic view of an example circuit board of the example container of FIG. 2.

FIG. 5 illustrates an example monitoring system 500, which may include an electronics module having one or more of the circuit elements 60 included on one or more circuit boards, such as the printed circuit board 62. Monitoring system 500 includes one or more sensors 502 coupled to a controller 504. The controller 504, in one example, is operably coupled to a communication module 506 to send and, in some examples, receive communications. Additionally, the controller 504 can be configured to selectively operate a clog remover 508 coupled to the turbine 82 or the separate source of negative pressure to help remove clogs of fibrin, clots, or other materials that may build up in the drain lumen.

Sensors 502 can include one or more sensors such as a color sensor 512 to detect color of the fluid in the cartridge, volume sensor 514 to detect the volume of the fluid in the cartridge 40, and an inertial motion sensor 516 to determine the orientation of the container 30. Sensors can be configured from one or more circuit elements, such as photodiodes, light emitting diodes, or other electronic components, as well as mechanisms to provide signals for the controller 504 to interpret as information regarding parameters of the fluid in the container 30 or other parameters.

The controller 504 can selectively receive a signal from the color sensor 512 to determine whether the drainage fluid is clear, cloudy, yellowish, or includes blood. Information regarding the color of serous fluid or the fluid collected may correlate to infection. In one instance, an unexpected change of color serous fluid along with an increase in serous fluid excretion may be indicative of an infection or a patient not healing properly. The color sensor 512 can include photodiodes configured to include red, green, or blue (RGB) filters to receive color signals. For example, a light filter of a selected color can be placed proximate each photodiode or a set of photodiodes on the drain hub to include a set of RGB light filtered photodiodes. In one example, the color sensor 512 can further include a light source to illuminate the fluid and produce a light signal for the photodiodes. The controller 504 can receive signals from the photodiodes with light filters and process the signals with information on the light source such as color of the light source or intensity of the light source to interpret the signals from the photodiodes with filters each time the signals from the photodiodes with filters are provided or sampled. In one example, the controller 504 can be configured to illuminate the light source a d sample the photodiodes with filters of the color filter if the ambient light is such that it will not interfere with the signals from the photodiodes with filters, such as when no ambient light is present.

In one example, the volume sensor 514 can include an array of photodiodes in a selected orientation or configuration, such as vertically extending from the bottom surface B toward the top surface T disposed to detect the presence of fluid in the cartridge. The location or enumeration of the photodiode detecting a presence of fluid next to the location or the enumeration of a photodiode not detecting a presence of fluid can be interpreted as a level of the fluid therebetween. The location or enumeration of the respective photodiodes detecting can be converted into a volume measurement via the controller 504. In some examples, a temperature measurement of the fluid can be received in cases in which temperature change of the fluid could affect fluid volume or used to calibrate a fluid volume measurement. In one example, at least one additional array of photodiodes may be arranged in a different orientation or configuration than the first orientation or configuration of photodiodes, such as configured along the bottom surface B or along an axis generally parallel with the bottom surface B. This way, the volume measurement can be taken in more than one orientation of the cartridge 40. A determination of volume via a volume measurement, for example, can be taken if the patient is sitting up or standing in a first orientation or laying down in second orientation in case the patient is in one orientation or the other for a prolonged period of time. The photodiodes can be disposed to be visible within a large sensor window 84. In one example, the sensor window 84 can be configured as a cross, either with right angles to the arrays of sensors in the window or with other angles as determined appropriate, and each set of photodiodes on the drain hub 42 visible within the cross. For example, a first set of photodiodes can be disposed in a first arm of the sensor window cross to measure fluid volume in the first orientation, and the second set of photodiodes to measure fluid volume in the second orientation can be disposed in the other arm of the cross.

The printed circuit board 62 can include a nine-axis microelectromechanical system (MEMS) inertial motion sensor 516 that may include a three-axis gyroscope, three-axis accelerometer, and three-axis magnetometer to detect orientation of the container 30, which can be applied to determine whether to measure volume of fluid in the cartridge 40. If, for example, the cartridge 40 is upright or in a selected orientation, such as the sensor window 84 configured upright or vertically from the ground or other reference, controller 504 can selectively receive a signal from the volume sensor 514 to determine the amount of fluid in the cartridge 40. If more the sensors are configured to make a volume measurement in more than one orientation, than controller 504 can be configured to receive a measurement from one or other sensor arrays depending on a the orientation detected via the inertial motion sensor.

In one example, the sensors 502 can also include a flow sensor to detect an amount of flow of fluid into or out of the cartridge 40. For example, a flow sensor can be installed proximate the opening of the cartridge 40. The rate and time of fluid poured from the cartridge when emptied can be used to determine fluid volume within the cartridge 40. The flow sensor described above may be of a type relying on temperature fluctuation supplied through incorporation of an integral heating unit, or of a type utilizing electromagnetic induction. In other examples, an amount of flow can be detected inferentially with one or more other sensors, such as the volume sensor 514. For instance, the controller 504 can determine an amount of flow from a volume $v_0$ measured at a time $t_0$ and a volume $v_1$ measured at a subsequent time $t_1$. An amount of flow F of the fluid into the cartridge 40 can thus be calculated from $F=(v_1-v_0)/(t_1-t_0)$. Still further, the sensors 502 can include a temperature sensor, such as a thermocouple, which can be used to detect whether the patient is running a fever and other sensors. In some examples, a temperature measurement of the fluid can be received in cases in which temperature change of the fluid could affect fluid volume or used to calibrate a fluid volume measurement.

Alternatively, fluid volume can be detected via a small orifice and a drop counter sensor as part of sensors 502. By passing drained fluid through a small diameter orifice after the fluid is filtered, the fluid is made into consistent droplets that can then be counted by a photodiode or similar sensor. Fluid droplet size will be relatively consistent provided the viscosity of the fluid remains consistent as well, and by counting the number of droplets, the volume of fluid can be determined as a product of droplet volume by the number of droplets.

Fluid volume could also be detected via a float. The float would allow measurement of the upper surface of the collected fluid from which the volume could be determined based on knowledge of the cartridge 40 geometry. In one example, the height of the float is tracked using a capacitive wiper. In another example, the height of the float is tracked optically with a sensor positioned above the float. In yet another example, the float is suspended on a cantilever attached to a spring, such that displacing the float would generate a measurable force to the spring in addition to corresponding movement of an analog indicator. The inertial motion sensor 516 can be used to determine the orientation of the cartridge 40, and the float could be measured when the cartridge is in one or more selected orientations.

Still further, fluid volume can be detected via the capacitive wiper or other capacitive circuit. Measurements would be take in a semi-isolated, narrow sampling column in the cartridge 40 to reduce the effect of orientation on the signal. Electrical traces would be embedded or attached to the wall or walls of the column such that progressive increase of fluid depth corresponds linearly to an electrical signal. Such measurement may utilize a reference column in order to improve measurement accuracy.

Still another configuration to detect fluid volume can include a comparative measurement of two samples including a reference sample and a bulk sample. Intrinsic properties of the drained fluid can be inconsistent both across the patient population and across the duration of drain usage, with measurements dependent upon intrinsic properties calibrated to produce usable results. A reference sample with at least one given extrinsic value is used to develop a correction factor that can then be applied to a second measurement of the bulk sample. In one example, the reference sample is a standardized height column of drainage fluid, and the bulk sample is the remainder of the fluid. By utilizing a measurement signal that attenuates approximately linearly with depth, the effect of differences in fluid can be reduced and a proportion for bulk sample depth can be determined, and from this volume can be extrapolated by utilizing the known cross-section of the cartridge 40. Signals applicable to such a measurement system include absorption spectrometry, ultrasound, light intensity and scattering, capacitance, and impedance.

In some examples, one or more sensors 502 can be located on the drain system and remote from the container 30. For example, the thermocouple can be located on the drain 16 or tubing 18, which is embedded in the patient at the surgical site, and coupled to the controller via signal pathways such as wires or traces.

Controller 504 can include circuitry to receive and process signals from the sensors 502, provide output signals to the communications module 506 and clog remover 508, and receive and process signals from communication module 506. In one example, controller 504 can include a processor 520 and memory 522 as well as various analog-to-digital converters or digital-to-analog converters are applied to provide and receive signals to various components. Processor 520 can include a microcontroller for one or more embedded applications 524 in memory 522, such as a small computing device on a single integrated circuit including one or more processor cores, memory, and programmable input/output peripherals. Memory 522 can include nonvolatile or programmable memory, such as flash memory and one-time programmable read only memory (ROM), can be provided to include, for example, computer implemented instructions for controlling the processor 520, is also often included on a chip, as well as a typically small amount of volatile memory such as random access memory (RAM), to include, for example, computer implemented instructions and computer readable data for controlling the processor 520.

Processing of signals can be implemented in a combination of hardware and computer programming in controller 504. For example, the programming can be processor-executable instructions stored on at least one non-transitory machine-readable storage medium, such the memory 522. The hardware can include at least one processor 520 to execute the instructions 524 loaded or stored in memory 522. In some examples, the hardware can also include other electronic circuitry to at least partially implement at least one feature of the processing. The information generated from processing can be stored as data in the memory 522. This data can include information interpreted from the sensors 502 as well as other information regarding the patient, coefficients, times, information regarding the drain system 10 that may be used to process the signals received from the sensors or the communication module 506.

Controller 504 can determine, based on signals received from the volume sensor 514, whether there is enough fluid to process signals from the color sensor 512. Further, controller 504 can determine, based on signals from the inertial motion sensor 516, whether the container 30 is upright or selectively oriented to receive signals from the volume sensor 514 and the color sensor 512. Still further, the controller 504 can determine time of measurement to determine flow based on two or more volume measurements. Additionally, the controller 504 can determine based on flow measurements over time whether a clog may be present or whether the wound or surgical site 14 has stopped draining fluid.

If, for example, the controller 504 determines a clog is present in the container, the controller 504 may automatically provide a signal to the clog remover 508 to operate the turbine 82 or other mechanism to dislodge or remove the clog. Alternatively, or additionally, the controller 504 may provide a notification to the patient, caregiver, or a remote care center alerting the presence of a clog.

The communication module 506 can be configured to include a wireless-network connectivity microcontroller 530 for an embedded application 532 stored in memory 534, such as a small computing device on a single integrated circuit including a processor core, memory, and programmable input/output peripherals. Nonvolatile or programmable memory, such as flash memory and ROM, to include, for example, computer implemented instructions for controlling the module, is also often included on the chip, as well as a typically small amount of volatile memory such as additional RAM), to include, for example, computer implemented instructions and computer readable data for controlling the module. Optional features of the module can include input/output serial ports, such as universal asynchronous receiver/transmitter (UART) or other serial communication interfaces such as inter-integrated circuits (I2C). The communications module can include one or more network processors subsystems for network-on-a-chip having a dedicated processor and memory for radio, baseband, and media access control (MAC) with encryption features as well as embedded internet protocol suite (TCP/IP) and cryptographic protocols (TLS/SSL) stacks, hypertext transfer protocol (HTTP) server, and other network protocols.

Additionally, the communications module 506 can include a wireless-network antenna 536. The antenna 536 can be low profile and configured to conserve space within the drain hub 42. Example antennas include printed inverted F antennas, patch antennas, ceramic antennas, as well as other configurations.

In one particular example of the monitoring system 500, the controller 504 can periodically or intermittently determine whether to receive signals from the some of the sensors 502, particularly the color sensor 512 and volume sensor 514. For example, the controller can determine from signals provided the inertial motion sensor 516 whether measurements from the volume sensor 514 would be accurate and whether fluid is proximate the color sensor 512. If not, the controller 504 could reschedule measurements or wait until the next scheduled measurement to receive signals. If so, the controller 504 could receive measurements from the volume sensor 514 and the color sensor 512.

Signals representative of sensor measurements can be converted to useable information can be stored as data with other patient or relevant information within memory on the drain hub 42. In one example, the data, particularly data that is transmitted via communication module 506, is encrypted to protect patient health information. In one example, the encrypted data is deleted after it is transferred from the drain hub 42.

One aspect of the volume measurement could be used to determine if the fluid has reached a selected volume amount such as its volume limit within the cartridge 40. If so, the controller 504 could provide a message via communication system 506, via an indicator light or sound, or other notification, to the patient or caregiver to replace the full cartridge with a new and empty cartridge. The controller 504 can also be configured to detect the presence of the new and empty cartridge, via a volume measurement or other mechanism, and restart or reset the process of periodically or intermittently receiving signals from the sensors 502.

Similarly, a notification can be provided if signals received from the color sensor 512 are determined to be outside of parameters for a given time or changes in the color signal over a period of time are determined to be outside of parameters. In some examples, parameters can be stored in memory and compared via processor on monitoring system 500. In other examples, sensor signals can be transmitted to a remote computing device that processes the signals against parameters and provides a notification.

Figure 6:
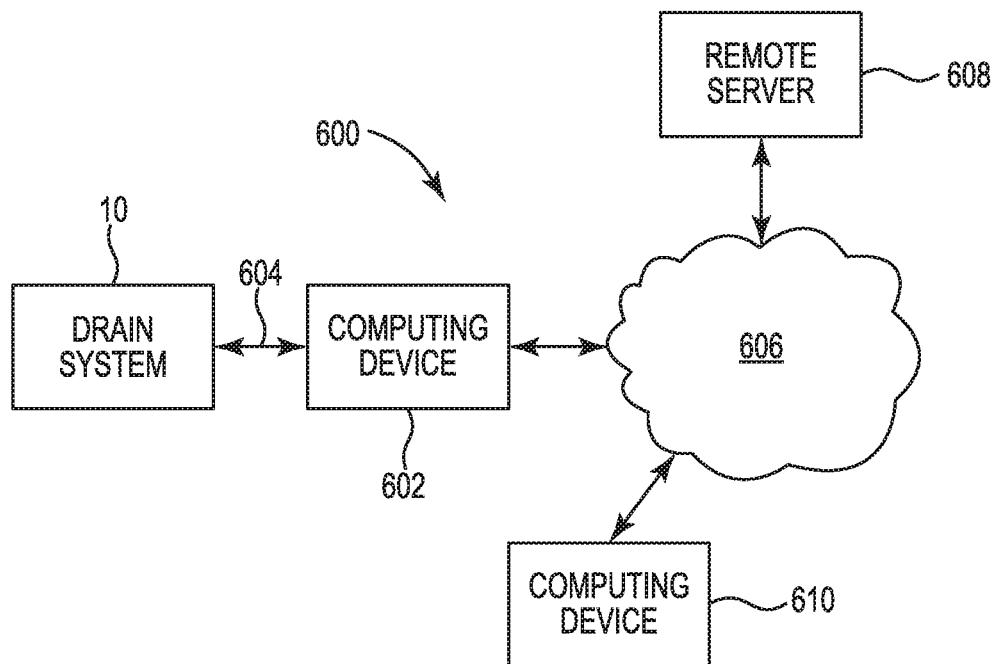
FIG. 6 is a schematic view of an example communication system including the example drain system of FIG. 1.

FIG. 6 illustrates an example communications system 600 for use with drain system 10. In the example, the communications module 506 of the drain system 10 can communicate directly with a computing device 602 over a wireless-network 604. The computing device 602 can be configured to exchange data from the drain system, or data processed from data from the drain system 10 via another communications network 606, e.g., a local area network or wide area network such as the Internet or other network, to a remote server 608. In one example, a computing device 610 can access the data related to the drain system 10 on the remote server 608 via an application over the communications network 606.

In one example, the communications module 506 of the container 30 can exchange computer data with computing device 602, which can include a mobile device, laptop, or network intermediary, via a wireless technology suitable for short distances. The computing device 602 can then exchange the computing data or additional processed data, over the communications network 606 to the remote server 608, which, in one example, is located in a data center. A clinician, the patient or caregiver can access the remote server via computing device 610, which can include a laptop, desktop, workstation, mobile device or other, or in some examples, via computing device 602.

The computing device 602 can include a general purpose mobile device such as a smartphone or tablet, laptop, or other computing device, or special purpose medical device configured to exchange data with the drain system 10. In this example, the computing device 602 can be provided with a computer program configured to relay data from the drain system 10 to the remote server 608 such as information processed from the sensors and, in some examples, receive information from the remote server and provide the information to the communications module 506, such as firmware updates. Additionally, the computer program can be configured to present data from the communications module in form usable by the patient or caregiver, such as a user interface that can alert the patient or caregiver to change the cartridge or other information. Also, the user interface can allow the patient or caregiver to interact with the drain system, such as controls that can operate the clog remover 508. Still further, the user interface can be configured to present information from the remote server.

Examples of wireless-networks 604 for use with the drain system 10 include wireless local area network (WLAN), wireless personal area networks (WPAN), wireless body area networks (WBAN) or other wireless networks for exchanging computer data over relatively short distances. In one example WLAN includes a wireless distribution method such as spread-spectrum or orthogonal frequency-division multiplexing (OFDM) radio within a limited area such as a home, school, office, or care center. Example WLANs include IEEE 802.11, which is a set of media access control (MAC) and physical layer (PHY) specifications for implementing WLAN computer communication in the 900 MHz and 2.4, 3.6, 5, and 60 GHz frequency bands created and maintained by the Institute of Electrical and Electronics Engineers (IEEE) LAN/MAN Standards Committee (IEEE 802). The communication standards and amendments can be implemented in products available under the trade designation Wi-Fi. One example WPAN exchanges data over short distances using short-wavelength ultra-high frequency radio waves in the industrial, scientific, and medical (ISM) band from 2.4 to 2.485 GHz (2402 and 2480 MHz or 2400 and 2483.5 MHz) based on frequency-hopping spread spectrum technology. Example WPANs and WBANs include IEEE 802.15, which is a set of wireless specialty network standards and can include products available under the trade designation Bluetooth. In one example, the WPAN network technology can include Bluetooth Low Energy, or Bluetooth LE, which might not be a backwards-compatible protocol with Bluetooth. In still another example, the communication protocol can include near-field communication (NFC) for low energy, passive-mode communication initiated with another communication device, such as a smartphone. In one example, the smartphone can include the initiator and the drain hub 42 can include the target to communicate with the initiator. In this manner, the drain hub 42 does not use energy from the battery 66 to communicate with the initiator.

The communications module 506 can be configured to exchange data in the wireless-network 604 with computing device 602 in several configurations. For example, the communications module 506 can be configured to exchange data in the wireless-network 604 with the computing device 602 via a networking device intermediary such as a wireless router or gateway, a communications device available under the trade designation CareLink Monitor from the present assignee, or other networking device. The communications module 506 can be configured to exchange data in the wireless-network 604 directly with the computing device 602 such as in a peer-to-peer configuration. In some examples, the communications module 506 can be selectively configured to exchange data with a computing device 602 via a networking device intermediary and/or peer-to-peer. At least certain, sensitive patient data such as patient health information may be encrypted as it is stored on the drain system 10, such as on a memory device on the drain hub 42. The memory device may be a persistent storage device such as a flash memory or other storage device. In case of the patient health information being transferred with the communication module 506, a secure connection or encryption is used to protect the data. To further protect the patient health data, data stored on the drain system 10 may be deleted after it is successfully transferred with the communication module 506. In one example, the communication module 506 may transfer the data, and then receive a confirmation from the computing device 602 via protocol that the data was successfully received. After receiving confirmation, the communication module 506 may initiate the controller 504 to begin a process of deleting the successfully transferred data. In one example, the process of deleting the successfully transferred data can be performed during periods of low sensor activity, periods of high battery capacity, or some other preferred period to reduce processing power of the controller 504 or improve battery capacity. The secured or encrypted patient data can be transferred again from the computing device 602 to the remote server 608. Once the data has been successfully transferred to the remote server 608 from the computing device 602, the data may be erased from the computing device 602 or the drain system 10 in a similar manner as deleting the data from the drain system 10 above.

In some examples, the computing device 602 can be replaced with a networking device intermediary such as the wireless router or gateway or the communications device available under the trade designation CareLink Monitor.

In one example, the computing device 610 can be provided with one or more computer programs of one or more computer programs, such as computer programs specifically configured for a patient or caregiver, computer programs specifically configured for clinicians, computer programs specifically configured for researchers, or other programs. In one example, computer programs can be configured to receive data such as information processed from the sensors. In another example, a computer program can be configured to receive telemetry data related to operation of the systems and applications of the drain system and not related to patient data. In one example, the computer program is a browser-based application. The computer program can be configured to present data from the communications module in form usable by the patient or caregiver or clinician, such as a user interface that can alert the patient or caregiver to change the cartridge 40 or other information that may present data differently or have addition functionality as a mobile application. Also, the user interface can allow the patient or caregiver to interact with the drain system 10, such as controls that can operate the clog remover 508.

Although the present disclosure has been described with reference to preferred embodiments, workers skilled in the art will recognize that changes can be made in form and detail without departing from the spirit and scope of the present disclosure.

What is claimed is:

1. A portable surgical drain system, comprising:
a subdermal drain at a first end of the portable surgical drain system, the subdermal drain configured to drain fluid from a surgical site; and
a container at a second end of the portable surgical drain system, the container in fluid communication with the subdermal drain providing a negative pressure to the subdermal drain, the container including a cartridge having a vacuity to draw and receive the fluid into the cartridge and a drain hub, the cartridge removably coupled to the drain hub to form the container, wherein the container includes at least one sensor disposed on the drain hub proximate a wall of the cartridge in which the at least one sensor is configured to detect from outside the cartridge at least one of fluid color, fluid volume in the cartridge, and orientation of the container, wherein the detection of the fluid volume and fluid color are based on whether the container is detected in a selected orientation.

2. The portable surgical drain system of claim 1 wherein the at least one sensor includes an inertial motion sensor to detect orientation of the container.

3. The portable surgical drain system of claim 1 including a processing circuit configured to receive signals from the at least one sensor.

4. The portable surgical drain system of claim 3 wherein the sensor includes a volume sensor to detect fluid volume in the container and the processing circuit is configured to determine fluid flow from the volume sensor.

5. The portable surgical drain system of claim 1 wherein the subdermal drain includes a lubricious coating.

6. The portable surgical drain system of claim 5 wherein the subdermal drain includes a lubricious coating on an inside surface and an outside surface.

7. The portable surgical drain system of claim 1 wherein the subdermal drain includes antimicrobial agents.

8. The portable surgical drain system of claim 7 wherein the subdermal drain includes an antimicrobial coating.

9. The portable surgical drain of claim 1 wherein the subdermal drain includes a heparin coating.

10. The portable surgical drain of claim 1 wherein the subdermal drain includes a drug eluding outside surface.

11. The portable surgical drain of claim 10 wherein the drug includes at least one of an antibiotic and anti-inflammatory agent.

12. The portable surgical drain system of claim 1 wherein the subdermal drain is fluidically coupled to the container via tubing.

13. The portable surgical drain system of claim 1 wherein the container is a suction source.

14. The portable surgical drain system of claim 13 wherein the container is set at a prescribed pressure.

15. A portable surgical drain system, comprising:
a subdermal drain at a first end of the portable surgical drain system, the subdermal drain configured to drain fluid from a surgical site; and
a container at a second end of the portable surgical drain system, the container in fluid communication with the subdermal drain providing a negative pressure to the subdermal drain, the container including a cartridge having a vacuity to draw and receive the fluid into the cartridge and a drain hub, the cartridge removably coupled to the drain hub to form the container, wherein the container includes at least one sensor disposed on the drain hub proximate a wall of the cartridge in which the at least one sensor is configured to detect fluid color, fluid volume in the cartridge from outside the cartridge, and orientation of the container, wherein the detection of the fluid volume and fluid color are based on whether the container is detected in a selected orientation; wherein the drain includes a suction member in fluid communication with the container and an inflatable balloon isolated from fluid communication with the container.

16. The portable surgical drain system of claim 15 wherein the inflatable balloon is distal the suction member.

17. The portable surgical drain system of claim 15 having a separate lumen in fluid communication with the inflatable balloon, wherein the separate lumen is not in fluid communication with the container.

18. The portable surgical drain system of claim 15 having a valve to selectively open and close the separate lumen.

19. The portable surgical drain system of claim 18 wherein the balloon is configured to be selectively inflated within the patient to hold the drain within the surgical incision and further configured to be selectively subsequently deflated to remove the drain from the patient.

20. The portable surgical drain system of claim 15 wherein the drain includes a lubricious coating.

21. The portable surgical drain system of claim 20 wherein the drain includes a lubricious coating on an inside surface.

22. The portable surgical drain system of claim 20 wherein the drain includes antimicrobial agents.

23. The portable surgical drain of claim 22 wherein the drain includes a heparin coating.

24. A container for a portable surgical drain system to receive a fluid from a drain at a surgical site, the container comprising:
a drain hub having a side and a sensor, the side including a sensor window and the sensor being disposed proximate an interior of the side and the sensor window; and
a cartridge removably coupled to the drain hub in fluid communication with the drain, the cartridge having a vacuity to draw and receive the fluid from the surgical site;
the cartridge disposed against an exterior of the side and the sensor window wherein the sensor includes an array of photodiodes on the drain hub to detect fluid volume and fluid color in the cartridge, wherein the detection of fluid volume and fluid color are based on whether the container is detected in a selected orientation.

25. The container of claim 24 wherein the drain hub includes a processing circuit configured to receive signals from the sensor.

26. The container of claim 25 wherein the drain hub includes a communications module operably couplable to a computing device via a wireless-network to exchange computer data between the processing circuit and the computing device.

27. The container of claim 25 wherein the drain hub includes a plurality of sensors including an inertial motion sensor and the volume sensor.

28. The container of claim 27 wherein the array of photodiodes are configured to detect fluid volume in the cartridge during a selected orientation of the cartridge and the processing circuit is configured to receive a signal from the volume sensor when the container is in the selected orientation as determined from a signal from the inertial motion sensor.

29. The container of claim 28 wherein the volume sensor includes another array of photodiodes configured to detect fluid volume in the cartridge during another selected orientation of the cartridge and the processing circuit is configured to receive a signal from the volume sensor when the container is in the another selected orientation as determined from a signal from the inertial motion sensor.

30. The container of claim 25 wherein the processing circuit is configured to provide an alert when the cartridge is filled to a selected volume of fluid.

31. The container of claim 24 wherein the cartridge is set at a prescribed pressure.

32. The container of claim 24 wherein the drain hub includes a fluid pathway configured to be in fluid communication with the drain and the cartridge, wherein the fluid pathway includes a turbine configured to be rotated about an axis within the fluid pathway.

33. A container for a portable surgical drain system to receive a fluid from a drain at a surgical site, the container comprising:
a drain hub having a side and sensor, the side including a sensor window and the sensor being disposed proximate an interior of the side and the sensor window; and
a cartridge removably coupled to the drain hub in fluid communication with the drain to draw and receive the fluid from the surgical site;
the cartridge disposed against an exterior of the side and the sensor window wherein the sensor includes a set of light filtered photodiodes and a light source on the drain hub to detect color of the fluid in the cartridge, wherein the detection of color of the fluid is based on whether the drain hub is detected in a selected orientation.

34. The container of claim 33 wherein the drain hub includes a processing circuit configured to receive signals from the sensor.

35. The container of claim 34 wherein the drain hub includes a communications module operably couplable to a computing device via a wireless-network to exchange computer data between the processing circuit and the computing device.

36. The container of claim 34 wherein the processing circuit is configured to provide an alert when the color of the fluid in the cartridge changes over a period of time.

37. A container for a portable surgical drain system to receive a fluid from a drain at a surgical site, the container comprising:
a drain hub having a side, a sensor, and a processing circuit operably coupled the sensor, the side including a sensor window and the sensor being disposed proximate an interior of the side and the sensor window; and
a cartridge removably coupled to the drain hub in fluid communication with the drain to draw and receive the fluid from the surgical site;
the cartridge disposed against an exterior of the side and the sensor window wherein the sensor to detect fluid color and fluid flow wherein the detection of fluid color and fluid flow are based on whether the drain hub is detected in a selected orientation and wherein the processing circuit is configured to provide an alert of a change in fluid color or increase in fluid flow.

38. The container of claim 37 wherein the drain hub includes a communications module operably couplable to the processing circuit, the communications modules coupled to a computing device via a wireless-network to exchange computer data between the processing circuit and the computing device.

39. The container of claim 37 wherein the sensor to detect fluid flow detects change of fluid volume over time.

40. The container of claim 37 wherein the sensor to detect fluid color includes an set of light filtered photodiodes and a light source on the drain hub to detect color of the fluid in the cartridge.

41. The container of claim 37 including a sensor to detect fluid color and a sensor to detect fluid flow.

42. The container of claim 41 wherein the sensor to detect fluid flow includes an array of photodiodes on the drain hub to detect fluid volume in the cartridge at multiple times.

43. A container for a portable surgical drain system to receive a fluid from a drain at a surgical site, the container comprising:
a drain hub having a side and a plurality of sensors, the side including a sensor window and a sensor of the plurality of sensors being disposed proximate an interior of the side and the sensor window; and
a cartridge removably coupled to the drain hub in fluid communication with the drain to draw and receive the fluid from the surgical site;
the cartridge disposed against an exterior of the side and the sensor window wherein a first sensor of the plurality of sensors includes a first volume sensor to detect volume of the fluid when the cartridge is in a first orientation, a second sensor of the plurality of sensors includes a second volume sensor to detect volume of the fluid when the cartridge is in a second orientation, and a third sensor of the plurality of sensors is an inertial motion sensor to detect whether the cartridge is in the first orientation or the second orientation, and a fourth sensor to detect color of the fluid, wherein the detection of color of the fluid is based on whether the cartridge is detected in a selected one of the first orientation and the second orientation.

44. The container of claim 43 wherein the first volume sensor includes a first array of photodiodes on the drain hub in a first configuration and the second volume sensor includes a second array of photodiodes on the drain hub in a second configuration.

45. The container of claim 43 wherein the inertial motion sensor includes a nine-axis microelectromechanical system.

46. The container of claim 43 wherein the cartridge is a pumpless cartridge.

47. A container for a portable surgical drain system to receive a fluid from a drain at a surgical site, the container comprising:
a drain hub having a side and at least one sensor, the side including a sensor window and the sensor being disposed proximate an interior of the side and the sensor window; and
a cartridge having a generally rigid vessel, the cartridge removably coupled to the drain hub in fluid communication with the drain to provide a suction source to draw the fluid from the surgical site into the vessel;
the cartridge disposed against an exterior of the side and the sensor window wherein the at least one sensor to detect a characteristic of the fluid in the vessel, the detected characteristic including fluid color, wherein the detection of fluid color is based on whether the drain hub is detected in a selected orientation.

48. The container of claim 47 wherein the characteristic the at least one sensor detects includes at least one of fluid color, fluid volume in the vessel, and orientation of the container.

49. The container of claim 47 wherein the suction source is a negative pressure.

50. The container of claim 49 wherein the suction source is a prescribed vacuity in the cartridge.

51. The container of claim 47 wherein the at least one sensor includes an array of photodiodes to detect fluid volume in the cartridge.

52. The container of claim 47 wherein the at least one sensor includes a float to detect fluid volume in the cartridge.

53. The container of claim 47 wherein the at least one sensor includes a capacitive sensor to detect fluid volume in the cartridge.

54. The container of claim 47 wherein the at least one sensor includes a photodiode operably coupled to a processing circuit to count droplets of fluid into the vessel to detect fluid volume in the cartridge.

55. The container of claim 47 wherein the cartridge includes an expandable vessel to provide the suction source.

56. The container of claim 47 wherein the cartridge includes a plurality of fluidically coupled vessels at separate negative pressures.

* * * * *